US00PP16291P3

(12) United States Plant Patent
McKenry

(10) Patent No.: US PP16,291 P3
(45) Date of Patent: Feb. 28, 2006

(54) GRAPE PLANT NAMED 'RS-3'

(50) Latin Name: *Vitis champinii×(Vitis riparia×Vitis rupestris)*
Varietal Denomination: RS-3

(75) Inventor: Michael McKenry, Fresno, CA (US)

(73) Assignee: The Regents of the University of California, Oakland, CA (US)

( * ) Notice: Subject to any disclaimer, the term of this patent is extended or adjusted under 35 U.S.C. 154(b) by 198 days.

(21) Appl. No.: 10/656,532

(22) Filed: Sep. 4, 2003

(65) Prior Publication Data

US 2005/0055749 P1 Mar. 10, 2005

(51) Int. Cl.
*A01H 5/00* (2006.01)

(52) U.S. Cl. ..... Plt./205
(58) Field of Classification Search ..... Plt./205
See application file for complete search history.

(56) References Cited

PUBLICATIONS

FPMS Grape Program Newsletter [online]. October 2001 [retrieved on Aug. 9, 2004]. Retrieved from the Internet: <http://fpms.ucdavis.edu/Grape//GrapeNewsletterOct2001.html>.*

Anwar, Safdar A. et al.; "Developmental Response of a Resistance–Breaking Population of *Meloidogyne arenaria* on *Vitis* SPP."; 2002, *Journal of Nematology,* vol. 34, No. 1, pp. 28–33.

Anwar, Safdar A. et al.; "Penetration and Development of *Meloidogyne arenaria* on Two New Grape Rootstocks"; 2002, *Journal of Nematology,* vol. 34, No. 2, pp. 143–145.

Anwar, Safdar A. et al.; "A Search for More Durable Grape Rootstock Resistance to Root–knot Nematode"; 2002, *Am. J. of Enology and Viticulture,* vol. 53, No. 1, pp. 19–23.

Anwar, Safdar A. et al.; "Penetration, Development and Reproduction of Meloidogyne Arenaria on Two New Resistant *Vitis* SPP."; 2000, *Nematropica* vol. 30, No. 1, pp. 9–17.

McKenry, M.V. et al.; "Interactions of Selected Rootstocks with Ectoparasitic Nematodes", 2001, *Am. J. Enol. Vitic.,* vol. 52, No. 4, pp. 304–309.

McKenry, M.V. et al.; "Interactions of Selected *Vitis* Cultivars with Endoparasitic Nematodes"; 2001, *Am. J. Enol. Vitic.,* vol. 52, No. 4, pp. 310–316.

* cited by examiner

*Primary Examiner*—Anne Marie Grunberg
*Assistant Examiner*—June Hwu
(74) *Attorney, Agent, or Firm*—Townsend and Townsend and Crew LLP

(57) ABSTRACT

A new and distinct grape plant (*Vitis vinifera* L. species), 'RS-3', which is useful as a rootstock, is distinguished by providing broad resistance to nematodes.

3 Drawing Sheets

Latin name of genus and species claimed: Interspecific variety of *Vitis champinii*×(*Vitis riparia*×*Vitis rupestris*).

Variety denomination: The name of the variety claimed is 'RS-3'.

BACKGROUND OF THE INVENTION

The invention relates to a new and distinct variety of the *Vitis* L. with broad nematode resistance.

The new variety is the result of an interspecific cross of the grape varieties 'Ramsey' (*Vitis champinii*) and 'Schwarzmann' (*Vitis riparia*×*Vitis rupestris*). 'RS-3' plants were asexually reproduced in Parlier, Calif. by the rooting of callused cuttings from dormant, lignified canes in spring or the rooting of green shoots under greenhouse mist in summer. 'RS-3' is a stable cultivar and reproduces true to type in successive generations of asexual reproduction.

BRIEF SUMMARY OF THE INVENTION

The present invention provides a novel grape having the characteristics described and illustrated herein. The grape variety, 'RS-3', exhibits broad resistance to nematodes and can be used as a rootstock.

DETAILED DESCRIPTION OF THE INVENTION

Figure 1:
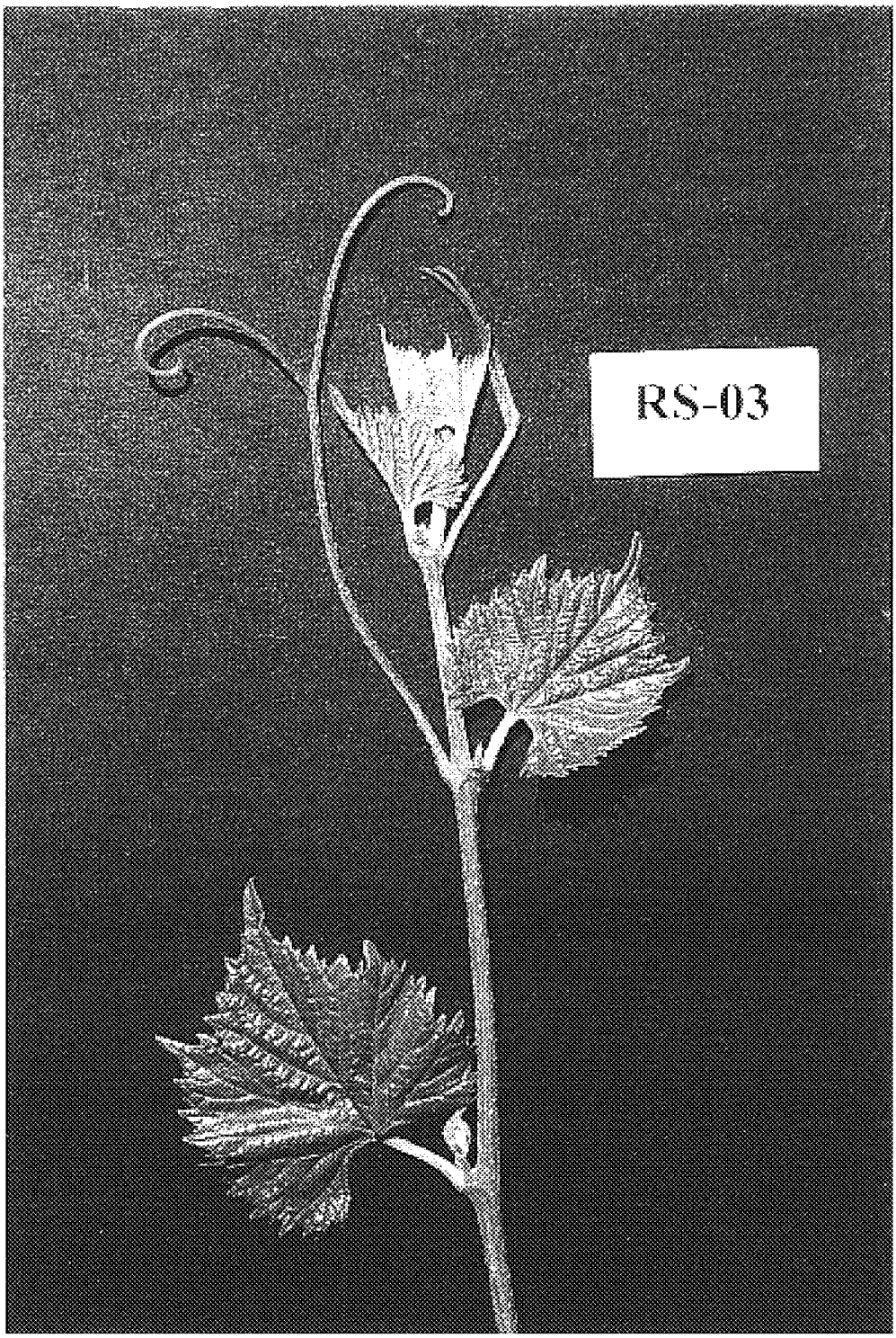
FIG. 1 illustrates a close-up photo of the 'RS-3' shoot tip.
Figure 2:
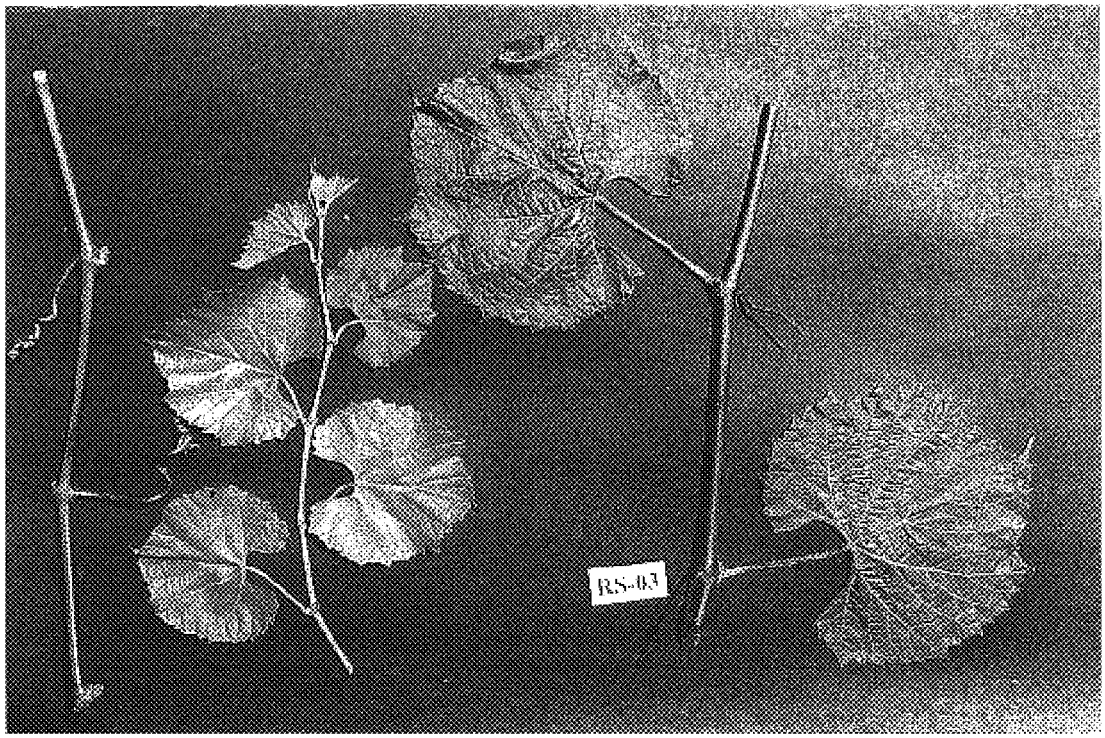
FIG. 2 illustrates a two-node section of primary shoot (upper, exposed side of mid shoot) with leaves attached (far right), section of primary shoot (lower, non-exposed side) (far left), and lateral shoot from the same portion of the primary shoot (center of photo).
Figure 3:
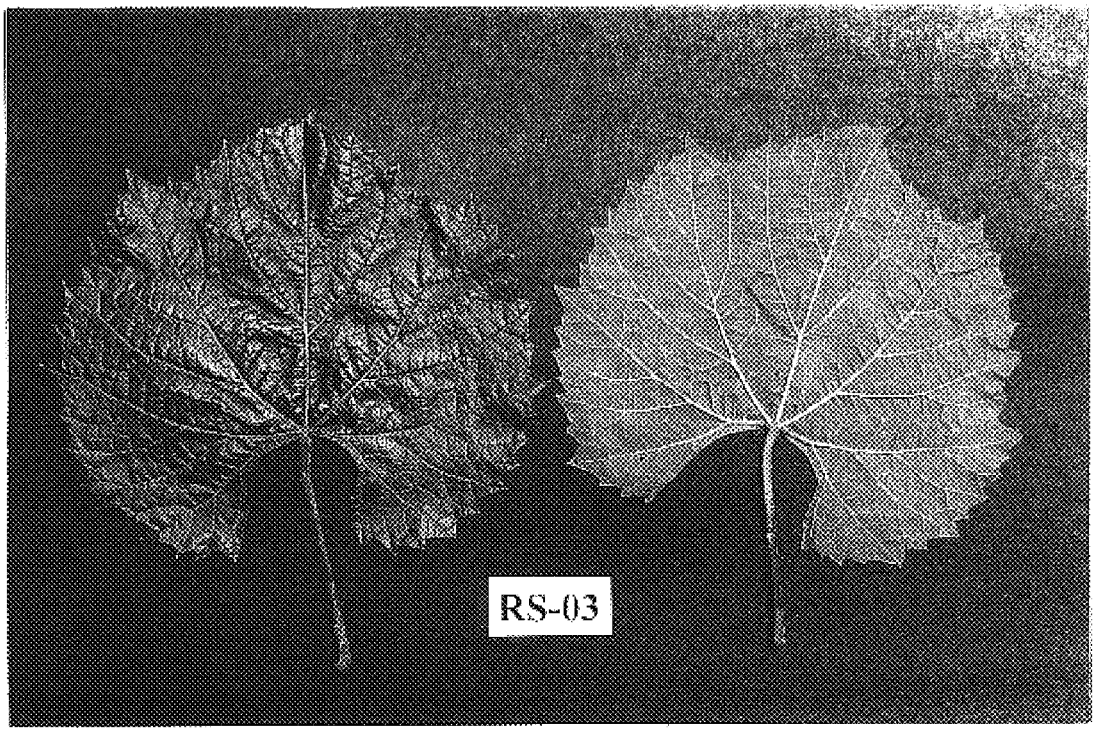
FIG. 3 illustrates an upper (left) and lower (right) sides of leaves from a primary 'RS-3' shoot.
Figure 4:
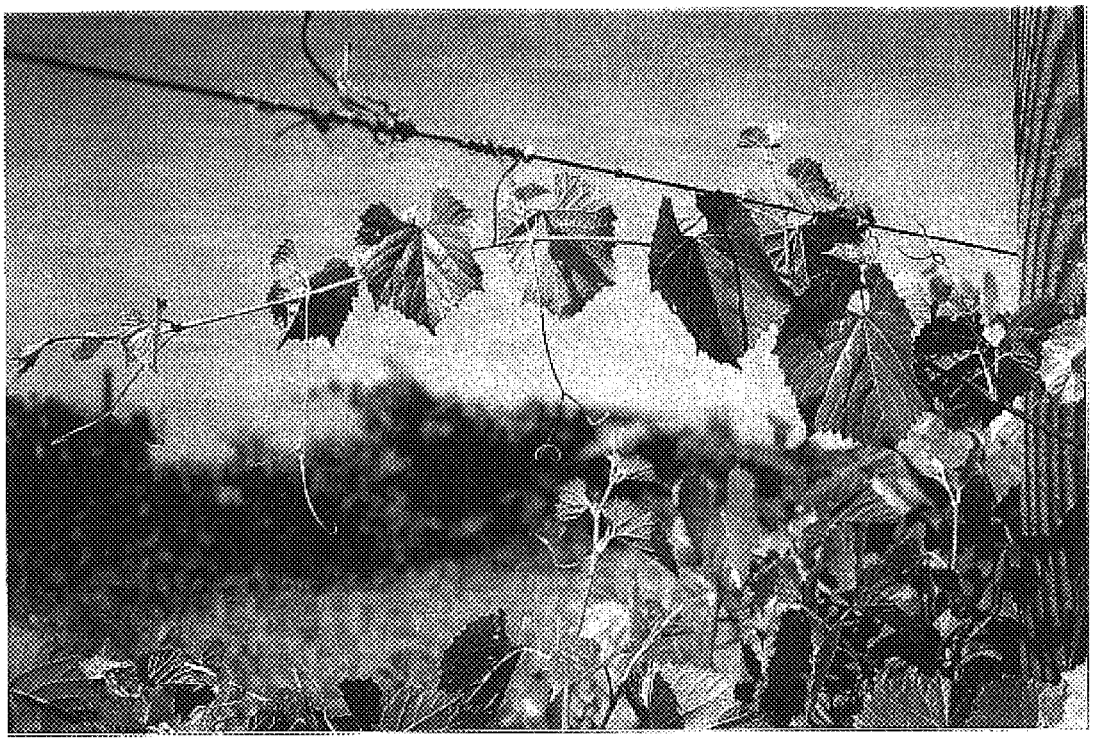
FIG. 4 illustrates a 'RS-3' trailing shoot attached to a trellis wire.

'RS-3' exhibits resistance to all known aggressive populations of root knot nematode (Anwar, S. and M. McKenry. *Nematropica* 30 (1):9–17 (2000)). Its resistance to ring nematode is slightly less than 'RS-2', but it also exhibits useful resistance to *Xiphenema index,* and root lesion, *Pratylenchus vulnus.* 'RS-3' is slightly susceptible to citrus nematode, *Tylenchulus semipenetrans.*

The resistance levels of 'RS-3', 'RS-2', 'Teleki 5C' and 'Ramsey' rootstocks to populations of *Meloidogyne incog-*

*nita* R3, *M. chitwoodi,* mixed *Meloidogyne* spp., *Meloidogyne* sp. pt. 'Ramsey' and two resistance-breaking populations of *M. arenaria* were compared in microplots. 'Freedom' and 'Harmony' rootstocks were also included as commercially resistant checks and 'Cabernet Sauvignon' was included as a susceptible check. Each replicate was inoculated by adding field soil containing each nematode population. The level of resistance was determined by comparing final population levels of J2 in soil and number of females and eggs per gram of root over the last two years. All rootstocks suppressed reproduction of the common *Meloidogyne* spp., however only 'RS-3' and 'RS-2' suppressed reproduction by the two resistance-breaking populations of *M. arenaria*. See, Tables 1–2. These data indicate that 'RS-3' exhibits a more durable root-knot resistance than commercially available rootstocks.

TABLE 1

Reproduction (eggs/g root) of six root-knot nematode populations on roots of seven grape rootstocks.

| Rootstocks | *M. arenaria** pt. Freedom | *M. arenaria* pt. Harmony | *Meloidogyne* spp. pt. Ramsey |
|---|---|---|---|
| 'Cabernet Sauvignon' | 2431a | 479a | 2239a |
| 'Ramsey' | 522a | 486a | 10bc |
| 'Teleki-5C' | 1135a | 98a | 43b |
| 'Freedom' | 1176a | 748a | 1c |
| 'Harmony' | 247a | 35ab | 3bc |
| 'RS-2' | 213a | 45ab | 1bc |
| 'RS-3' | 92ab | 1b | 2bc |

| Rootstocks | *M. incognita* | Mixed *Meloidogyne* spp. | *M. chitwoodi* |
|---|---|---|---|
| 'Cabernet Sauvignon' | 288a | 239a | 7abc |
| 'Ramsey' | 4b | 6b | 148ab |
| 'Teleki-5C' | 14b | 25ab | 322a |
| 'Freedom' | 8b | 1b | 119ab |
| 'Harmony' | 1b | 2b | 38abc |
| 'RS-2' | 1b | 4b | 6abc |
| 'RS-3' | 1b | 4b | 15abc |

*Statistical analysis based on Log (n + 1) transformed data. Back transformed means are shown.
Means of three replications. Means within a column followed by the same letter are not significantly different at P = 0.05.
Mixed *Meloidogyne* spp. includes *M. incognita, M. arenaria* and *M. javanica*.

TABLE 2

Reproduction (J2/250 $cm^3$ soil) of five root-knot nematode populations on roots of nine grape rootstocks.

| Rootstocks | *M. arenaria** pt. Freedom | *M. arenaria* pt. Harmony | *Meloidogyne* spp. pt. Ramsey |
|---|---|---|---|
| 'Cabernet Sauvignon' | 298a | 78a | 650a |
| 'Ramsey' | 180a | 10abc | 6b |
| 'Freedom' | 87ab | 42ab | 6b |
| 'Teleki 5c' | 52ab | 15abc | 11b |
| 'RS-2' | 39ab | 30ab | 5b |
| 'RS-3' | 10bc | 3bc | 5b |

| Rootstocks | Mixed *Meloidogyne* spp. | *M. chitwoodi* |
|---|---|---|
| 'Cabernet Sauvignon' | 1035a | 596a |
| 'Ramsey' | 3bc | 3bc |
| 'Freedom' | 2bc | 5bc |
| 'Teleki 5c' | 2bc | 9b |
| 'RS-2' | 2bc | 2bc |
| 'RS-3' | 5bc | 43b |

*Statistical analysis based on Log (n + 1) transformed data. Back transformed means are shown.
Means of three replications. Means within a column followed by the same letter are not significantly different at P = 0.05.
Mixed *Meloidogyne* spp. includes *M. incognita, M. arenaria* and *M. javanica*.

'RS-3' generally imparts slightly less scion vigor than 'RS-2', its sibling. In sandy, frequently-irrigated soils, 'RS-3' imparts ⅔ the vigor and yield of variety 'Freedom'. The full range of soil and climate preference of 'RS-3' is unknown.

A botanical description of 'RS-3' is provided below based on observations and measurements made during the period of April 10 to Aug. 1, 2003 at the University of California Kearney Agricultural Center, 9240 S. Riverbend Avenue, Parlier, Calif. 93648 (Riverbend Avenue, between Manning and Dinuba Avenues, Fresno County). 'RS-3' rootstock was approximately 10 years old when observed. The vines were irrigated by drip irrigation and row centers were cultivated by disk twice each year. Berms were hand hoes or treated with paraquat contact spray. Color terminology used in the following description is based on the scheme described in Aloy, John Maerz and M. Rea Paul. A dictionary of color, $2^{nd}$ edition. McGraw-Hill Book Co., New York, 1950. Descriptors for the guidelines for Grapevine (*Vitis.* L), International Union for the Protection of New Varieties of Plants, Geneva, Switzerland are provided.

Vine: Very vigorous, horizontal in attitude (U.P.O.V. — 6.1.5/5), climbing readily on support wires. Bud burst early (U.P.O.V — 7.1.2/3).

Shoots:

*Shoot tip.*—Closed (U.P.O.V. — 6.1.1/1), globular, downy white.

*Young leaves.*—Light yellowish-green (U.P.O.V — 6.1.16/1)(Plate 20, H-5) with white (U.P.O.V. — 6.1.2/1), medium dense prostrate hairs (U.P.O.V. — 6.1.3/5).

*Internodes.*—Red (Plate 4, F-2) with green stripes on the exposed, dorsal side (U.P.O.V. — 6.1.6/2) and green with few red stripes on the ventral side (U.P.O.V. — 6.1.7/2) in the spring, becoming light pink in midsummer on the dorsal side and light green on the ventral side. Sparse prostrate hairs (U.P.O.V. — 6.1.11/1). Relief of surface is striate. Length ranges between 11 and 16 cm, averaging 12.45 cm. Width ranges between 5 and 7 mm, averaging 6.2 mm.

*Nodes.*—Coloration is similar to internodes (U.P.O.V. — 6.1.8/2 and U.P.O.V. — 6.1.9/2). Width ranges between 7 and 10 mm, averaging 9.2 mm. Buds average in size, not prominent.

Tendrils: Intermittent, 0-0-2-0-2-0-2 (U.P.O.V. — 6.1.14/1). Mostly red (more so at tips) with some green in the spring; becoming pinkish green in midsummer. Forked. Length is long, ranging between 12 and 21 cm, averaging 17.46 cm (U.P.O.V. — 6.1.15/7). Width ranging between 1 and 2 mm, averaging 1.5 mm. Tendril color: Red (Plate 4, F-2) on the dorsal, exposed side and pinkish red (Plate 5, I-5)

on the underside, becoming light pink (Plate 4, H-3) on midsummer growth.

Flowers: Male with reflex stamens and no gynoecium (U.P.O.V. — 6.2.1/1 and 4). Flower clusters range in length between 4.5 and 12 cm.

RS-3 plants do not produce complete flowers; they only contain male parts. No fruit is produced. The average date of the beginning of bloom is May 2 at Parlier, Fresno County, Calif. The period of bloom lasts 7 to 10 days, depending on the season. The flowers abscise as bloom begins and the flower cluster dries up.

Leaves, blades:

*Shape.*—Reniform (U.P.O.V. — 6.1.22/5), almost entire (U.P.O.V. — 6.1.23/1). Open, U shaped petiolar sinus (U.P.O.V. — 6.1.30/3) without exposed veins (U.P.O.V. — 6.1.32/1).

*Size.*—Large (U.P.O.V. — 6.1.21/7). Length ranging between 12 and 15.5 cm, averaging 13.5 cm. Width ranging between 12 and 16 cm, averaging 13.8 cm.

*Appearance.*—Upper surface is glabrous and medium green (Plate 21, H-6). The light, yellowish green veins are prominent, with reddish-pink color on basal ⅓ of the main veins, becoming faint on midsummer growth (U.P.O.V. — 6.1.24/3). Lower surface is glabrous (U.P.O.V. — 6.1.23/1) and yellowish green (Plate 20, G-4) with sparse, prostrate hairs on the veins (U.P.O.V. — 6.1.38/3). Contour is flat (U.P.O.V. — 6.1.25/1). Surface is bullate (U.P.O.V. — 6.1.26/5).

*Dentation.*—Teeth wide, short (U.P.O.V. — 6.1.28/3), pointed with straight sides (U.P.O.V. — 6.1.27/2). P=0.33 (height/width) (U.P.O.V. — 6.1.27/3).

Leaves, petioles: Red (Plate 7, A-12) on dorsal (exposed) side and red with green stripes on ventral side, becoming pink on midsummer growth. Sparse, prostrate hairs. Length ranges between 5 and 8 cm, averaging 6.7 cm; width is 3 mm (U.P.O.V. — 6.1.40/2).

Canes (mature shoots): Lignified, mature shoots in late summer and fall are medium reddish-brown (U.P.O.V. — 6.1.42/4) with obvious striations (U.P.O.V. — 6.1.41/3) in the internodes. About every $4^{th}$ striation is dark brown, often resulting in 5 to 7 obviously darker striations per internode.

Trunk: The first inner layer of old bark is slightly grayish-brown (Plate 7, A-10). The outer layer is rough, peeling and gray (Plate 7, A-7) due to weathering and trunk expansion.

For purposes of comparison, a similar analysis of parents 'Schwarzmann' and 'Ramsey' performed at the USDA collection at California State University, Fresno. The following is a result of that analysis:

'RAMSEY' ROOTSTOCK

Vine: Vigorous, dense growth; upright in attitude.

Shoots:

*Shoot tip.*—Half open, felty white.

*Young leaves.*—Light, yellowish-green. Medium, prostrate hairs on upper surface. Medium, prostrate hairs on lower surface, especially on the veins and the petiole.

*Internodes.*—Light, yellowish-green. Medium, white tufted hairs or tomentum. Medium in length; small to medium in diameter. Relief of surface is slightly striate.

*Nodes.*—Coloration is similar to internodes. Fewer hairs than on internodes. Buds average in size, not prominent.

Tendrils: Intermittant, 0-0-2-0-2-0-2. Small to medium long and fine; bifurcated. Light, yellowish-green.

Flowers:

*Female.*—Small, compact clusters of medium-small black berries.

Leaves, blades:

*Shape.*—Reniform to almost round, slightly 3-lobed. Petiolar sinus deep, open U-shaped.

*Size.*—Medium to medium-small.

*Appearance.*—Upper surface medium dark green with light, prostrate hairs. Lower surface medium green with light green veins and moderate tufted tomentum. Contour is flat. Surface is smooth.

*Dentation.*—Teeth uniform, straight-sided to slightly concave, shallow and distinct.

Leaves, petioles: Light, yellowish-green with tufted tomentum. Medium in length.

Canes (mature shoots): Lignified, mature shoots in late summer and fall are brown with some darker striations in the internodes. Numerous short to medium lateral shoots are present.

Notable differences between 'RS-3' and 'Ramsey' include: 'RS-3' has horizontal vines whereas 'Ramsey' has vines upright in attitude. Shoot tips of 'RS-3' are typically closed whereas those of 'Ramsey' are half open. The leaf blades of 'RS-3' are large whereas those of 'Ramsey' are medium to medium-small. 'RS-3' shoots are red with green stripes on the dorsal side in the spring, becoming light pink in midsummer, whereas 'Ramsey' shoots (internodes and nodes) are light, yellowish-green. 'RS-3' flowers are male and abscise at bloom, whereas 'Ramsey' flowers are female and produce small fruit clusters.

'RS-3' petioles are red on the dorsal side in the spring, becoming pink on midsummer growth and 'RS-3' has sparse, prostrate hairs, whereas 'Ramsey' leaf petioles are light, yellowish-green with tufted tomentum.

'SCHWARZMANN' ROOTSTOCK

Vine: Vigorous, horizontal in attitude, climbing readily on support wires.

Shoots:

*Shoot tip.*—Closed, shiny green.

*Young leaves.*—Light, yellowish-green. Upper surface glabrous. Sparse, white, prostrate hairs on the petiole and the main veins on the lower surface.

*Internodes.*—Light, yellowish-green with violet-red and green stripes on the upper side. The red coloration becomes more faint in mid to late summer growth. Very sparse, white prostrate hairs. Medium in length and diameter. Relief of surface is slightly striate.

*Nodes.*—Coloration is similar to internodes. Glabrous. Buds average in size, not prominent.

Tendrils: Intermittant, 0-0-2-0-2-0-2. Fairly long and fine, bifurcated. Light, yellowish-green with violet-red coloration, especially on the branches.

Flowers: Male.

Leaves, blades:

*Shape.*—Orbiculo-reniform, entire or slightly 3-lobed. Petiolar sinus wide U-shaped.

*Size.*—Large.

*Appearance.*—Upper surface is glabrous and medium dark green. Lower surface is glabrous and medium light green with short hairs in the veins. Occasional light pink coloration on the main veins at the petiolar junction. Contour is flat. Surface is slightly bullate with more puckering at the petiolar junction. Dentation: teeth irregular, slightly convex, medium large and sharply pointed.

Leaves, petioles: Light, yellowish-green with light red coloration, especially on the upper side. The coloration is more faint in mid and late summer growth.

Canes (mature shoots): Lignified, mature shoots in late summer and fall are medium reddish-brown with striations in the internodes. Strong and long lateral shoots are present under high vigor conditions.

Notable differences between 'RS-3' and 'Schwarzmann' include: 'RS-3' has downy white shoot tips, whereas those of 'Schwarzmann' are yellowish-green. 'RS-3' has teeth on the leaves that are short, whereas those of 'Schwarzmann' are medium-large.

'RS-3' young leaves have medium dense prostrate hairs, whereas 'Schwarzmann' young leaves are glabrous with sparse hairs on the main veins on the lower surface.

'RS-3' leaf blades are reniform in shape, whereas 'Schwarzmann' leaf blades are orbiculo-reniform, sometimes slightly 3-lobed.

What is claimed is:

1. A new and distinct variety of grape plant having the characteristics described and illustrated herein.

* * * * *